United States Patent [19]
Nishide et al.

[11] Patent Number: 5,183,750
[45] Date of Patent: Feb. 2, 1993

[54] PROCESSES FOR THE PRODUCTION OF PHOSPHATIDIC ACID

[75] Inventors: Tsutomu Nishide; Daisuke Yasumura; Yoshinobu Nakajima, all of Ibaraki; Akiko Onodera, Hokkaido; Takuji Yasukawa, Ibaraki; Hirokazu Kokumai, Ibaraki; Tomoshige Umeda, Ibaraki; Seiji Nomura, Chiba; Hideki Mori, Ibaraki, all of Japan

[73] Assignee: Kao Corporation, Tokyo, Japan

[21] Appl. No.: 528,982

[22] Filed: May 25, 1990

[30] Foreign Application Priority Data

May 26, 1989 [JP] Japan .................................. 1-133653
May 26, 1989 [JP] Japan .................................. 1-133654
May 26, 1989 [JP] Japan .................................. 1-133655

[51] Int. Cl.$^5$ .......................... C12P 7/64; C12P 7/62; C12P 9/00; C12N 9/16
[52] U.S. Cl. ................................. 435/134; 435/135; 435/196; 435/151; 435/42
[58] Field of Search .............. 435/134, 135, 196, 131, 435/42

[56] References Cited

FOREIGN PATENT DOCUMENTS

0285421 3/1988 European Pat. Off. .
0311163 9/1988 European Pat. Off. .

OTHER PUBLICATIONS

Koso Handbook (Enzyme Handbook) p. 457 (1987).
J. Brewing Soc. Jpn. 82(2) 76–79 (1987).
Brauver et al., Plant Physiol., 92 (3), pp. 672–678, 1990.
Babenko et al., Dokl. Acad. Nauk SSSR, 313(2), pp. 478–482, 1990.
Nakayama et al., Ceral Chem., 58(4), 260–4, 1981.

*Primary Examiner*—David M. Naff
*Assistant Examiner*—Mike Meller
*Attorney, Agent, or Firm*—Sughrue, Mion, Zinn, Macpeak & Seas

[57] ABSTRACT

A process for the prodution of phosphatiolic acid is carried out by treating phospholipids with an enzyme capable of hydrolyzing a phospholipid into phosphatidic acid and a nitrogen-containing base and another enzyme capable of hydrolyzing a phospholipid into a diglyceride and a phosphoryl base. Further, another process for the production of phosphatidic acid is carried out by treating phospholipids with a treatment product of an oilseed is disclosed.

26 Claims, No Drawings

PROCESSES FOR THE PRODUCTION OF PHOSPHATIDIC ACID

FIELD OF THE INVENTION

The present invention relates to a process for the production of modified phospholipids. More particularly, it relates to a process for the production of modified phospholipids (unless otherwise noted, the expression "phospholipids" as used herein means phospholipids and/or a phospholipid mixture) which comprises treating phospholipids with an enzyme capable of hydrolyzing a phospholipid into phosphatidic acid (hereinafter, referred to as "PA") and a nitrogen-containing base and another enzyme capable of hydrolyzing a phospholipid into a diglyceride and a phosphoryl base.

The present invention further relates to a process for the production of modified phospholipids which comprises treating phospholipids with a treatment product of an oilseed. More particularly, it relates to a process for the production of phosphatidic acid which comprises hydrolyzing phospholipids with the use of a treatment product of an oilseed.

BACKGROUND OF THE INVENTION

Phospholipids, which are basic constituents of biomembranes, belong to lipids controlling basic life activities including protection of cellular tissues, transfer of information and controlling of the migration of substances.

Recently it has attracted scientific and industrial attention that vesicles or liposomes comprising a phospholipid capable of forming a bilayer membrane can include various functional substances. These vesicles are expected to be applicable to, for example, a drug delivery system (DDS) in the field of medicine and pharmacology.

We have studied the application of these highly functional lipids to the food industry and successfully developed a cooking oil showing no oil spattering and excellent release properties by using PA which is one of phospholipids (refer to JP-A-1-27431; the term "JP-A" as used herein means an "unexamined published Japanese patent application").

Examples of the industrial uses of PA include application of PA to foods for, e.g., improving dough properties in a baking process as described in JP-A-58-51853 (corresponding to U.S. Pat. No. 4,478,866), producing an emulsifier comprising PA and a zein complex as described in JP-A-62-204838; application of PA to drugs as described in JP-A-54-105222, JP-A-55-11582 (corresponding to Canadian Patent 1121829), JP-A-56-127308 and JP-A-60-255728; application of PA to cosmetics as described in JP-A-59-27809 (corresponding to U.S. Pat. No. 4,874,791); and application of PA to chemicals as described in JP-A-53-108503 and JP-A-60-243171. Thus the application of PA has been attempted in various fields.

However it is highly difficult to collect PA at a high purity, since PA per se is contained in a small amount in lecithin which is a side product obtained in the production of an oil. No method for the production of PA on an industrial scale has been established so far. Accordingly, the application range of PA is still restricted, compared with that of lecithin.

SUMMARY OF THE INVENTION

Under these circumstances, we have conducted extensive studies in order to overcome the above-mentioned problems and thus completed the present invention.

Accordingly, the present invention provides a process for the production of modified phospholipids which comprises treating phospholipids with an enzyme capable of hydrolyzing a phospholipid into phosphatidic acid and a nitrogen-containing base and another enzyme capable of hydrolyzing a phospholipid into a diglyceride and a phosphoryl base.

More particularly, the present invention provides a process for the production of PA from phospholipids which comprises hydrolyzing the phospholipids with the use of an enzyme capable of hydrolyzing a phospholipid into PA and a nitrogen-containing base and another enzyme capable of hydrolyzing a phospholipid into a diglyceride and a phosphoryl base, either separately or simultaneously, to thereby produce PA which has a high purity and a high solubility and contaminated with little side products such as unhydrolyzed matters.

The present invention further provides a process for the production of modified phospholipids which comprises treating the phospholipids with a treatment product of an oilseed. More particularly, it relates to a process of the production PA from phospholipids on an industrial scale which comprises hydrolyzing the phospholipids in a solvent comprising an organic solvent and/or an aqueous solution containing at least one substance selected from the group consisting of an alkali metal carboxylate, an alkaline earth metal carboxylate, a mixture of a carboxylic acid and an alkali metal salt and a mixture of a carboxylic acid and an alkaline earth metal salt with the use of the treatment product of the oilseed to thereby produce highly pure PA contaminated with little side products such as unhydrolyzed matters.

DETAILED DESCRIPTION OF THE INVENTION

Examples of the phospholipids to be used in the present invention include phosphatidylethanolamine (PE), phosphatidylcholine (PC), phosphatidylserine (PS), phosphatidylinositol (PI), phosphatidylglycerol (PG) and mixtures thereof.

These phospholipids may consist either the same or different fatty acids which may be either saturated or unsaturated and have 8 to 22 carbon atoms. Examples of the constituting fatty acids include caproic acid, capric acid, lauric acid, myristic acid, palmitic acid, stearic acid, behenic acid, arachidic acid, palmitoleic acid, oleic acid, linoleic acid, $\alpha$- and $\gamma$-linolenic acid, erucic acid, arachidonic acid, eicosapentaenoic acid, docosahexaenoic acid and tetracosaenoic acid. These phospholipids may be either extracts or concentrates of natural substances or synthetic ones, without limitation.

As the enzyme capable of hydrolyzing a phospholipid into PA and a nitrogen-containing base, phospholipase D (abbreviated as PL-D hereinafter) originating from a microorganism or a plant is preferable. As the enzyme capable of hydrolyzing a phospholipid into a diglyceride and a phosphoryl base, on the other hand, one or more enzymes selected from among phospholipase C (abbreviated as PL-C hereinafter), phosphodiesterase, acid phosphatase and alkali phosphatase, each originating from a microorganism, an animal or a plant, may be employed.

In the present invention, it is particularly preferable to use an enzyme, which specifically functions on phosphatidylinositol so as to hydrolyze a phospholipid into a diglyceride and phosphorylinositol, as the phospholipase C.

It is also possible to use the above-mentioned enzyme in the form of a fixed enzyme so as to sustain the activity thereof for a long time. Examples of the carrier for the fixation include cellulose, dextran, polystyrene, polyacrylamide, polyvinyl alcohol, ion exchange resins, magnetic substances, alumina, photo-crosslinked resins, alginates and various gelling agents. In the present invention, the above-mentioned enzyme or an extract containing the above-mentioned enzyme may be fixed on these carriers through, for example, adsorption, ionic bond, covalent bond or inclusion so as to give a fixed enzyme in the form of particles, a film or a sheet.

In the present invention, it is also possible to use a treatment product of an oilseed in addition to, or instead of the above-mentioned enzymes to produce modified phospholipids.

The oilseed which can be used in the present invention is disclosed, for example, in Yukagaku, vol. 37, No. 8, 581 to 587 (1988), and the specific Examples thereof include soybean (e.g., Glycine max Merrill), rapeseed (e.g., Brassica campetris L.), sunflower seed (e.g., Helianthus annuus L.), peanut (e.g., Arachis hypogea L.), cotton seed (e.g., Gossypium hirsutum L., G. barbadense L., G. herbaceum Oliv. or G. arboreum L.), safflower seed (e.g., Carthamus tinctorius L.), mustard seed (e.g., Brassica juncea Czern.), sesame seed (e.g., Sesamum indicum L.), olive seed (e.g., Olea europaea) and corn (e.g., Zea mays L.). Among these oilseeds, soybean is preferable.

Further, oilseeds collected from lipoxygenase-deficient plants as described, for example, in Nippon Shokuhin Kogyo Gakkaishi, vol. 31, No. 11, 751 to 758 (1984), Nippon Shokuhin Kogyo Gakkaishi, vol. 33, No. 9, 653 to 658 (1986) and Nippon Jozo Kyokaishi, 82, 76 to 79 (1987) are preferably used in the present invention. Among them, a lipoxygenase-deficient soybean as described in Nippon Jozo Kyokaishi, 82, 76 to 79 (1987) is more preferable as the oilseed collected from the lipoxygenase-deficient plant, though it is not restricted thereby.

In the present invention, it is preferable to use these oilseeds in the form of a ground matter or an extract thereof as the treatment product of the oilseed, and they can be used either alone or a mixture of them.

The ground matter of the oilseed may be obtained by grinding the above-mentioned oilseed by a physical treatment and it can be employed in the production of modified phospholipids as such. The particle size of the ground matters may be preferably 5 mm or below, though it is not restricted thereby. Any devices and means known in the art may be employed for the grinding.

On the other hand, the extract of the oilseed may be obtained by grinding the above-mentioned oilseed by a physical treatment (the particle size of the ground matters may be preferably 5 mm or below, though it is not restricted thereby) and extracting the ground matters thus obtained with water or an aqueous solution containing at least one compounds selected from the group consisting of an alkali metal carboxylate, an alkali metal salt and an alkaline earth metal salt.

In the alkali metal carboxylate, the alkali metal salt and the alkaline earth metal salt to be used in the extraction, the carboxylic acid may be selected from among straight chain or branched aliphatic carboxylic acids having 2 to 8 carbon atoms and aromatic carboxylic acids having 7 to 12 carbon atoms, for example, aliphatic carboxylic acids such as acetic acid, butyric acid, propionic acid and aromatic carboxylic acids such as benzoic acid. Examples of the alkali metal include sodium and potassium while examples of the alkaline earth metal include barium, magnesium and calcium. As the alkali metal salts or the alkaline earth metal salts, halides, carbonates and phosphates of these metals can be used therefor.

In the extraction to be conducted in such a system, it is important to control the pH value of the extraction solvent. It is preferable to conduct the extraction at a pH value of from 4.0 to 7.5, more preferably at pH $6.0 \pm 1.0$.

The above-mentioned extraction may be conducted by combining physical extraction procedures such as allowing to stand, stirring and shaking with the use of the above-mentioned extraction solvent at a ratio by weight of from 0.1 to 50 (preferably from 1.0 to 20) based on the ground matter of the oilseed at a temperature of from 10° to 30° C. (preferably from 15° to 25° C.) for 1 to 24 hours (preferably for 1 to 12 hours).

The extract thus obtained may be used in the production of modified phospholipids as such.

Furthermore, the extract may be formulated into a liquid or a solid by adding stabilizer(s)such as sugars, proteins or various salts followed by concentrating under reduced pressure, drying or lyophilizing, if required.

To efficiently proceed hydrolyzation reaction in the production of modified phospholipids, it is preferable that the reaction is conducted in a solvent comprising an organic solvent and/or an aqueous solution containing at least one substance selected from the group consisting of an alkali metal carboxylate, an alkaline earth metal carboxylate, a mixture of a carboxylic acid and an alkali metal salt, or a mixture of a carboxylic acid and an alkaline earth metal salt. Further, more efficiently reaction rate can be obtained by hydrolyzation under the presence of an alkali metal salt and/or an alkaline earth metal salt.

The organic solvent to be used in the production of modified phospholipids of the present invention may be selected from among alkyl esters of carboxylic acids, alkanes, aliphatic hydrocarbons, alicyclic hydrocarbons, aromatic hydrocarbons, halogenated hydrocarbons and mixtures thereof, each having a melting point of 40° C. or below. Examples of alkyl carboxylates include alkyl (straight chain or branched alkyls having 1 to 8 carbon atoms) esters of straight chain or branched fatty acids having 2 to 6 carbon atoms, for example, methyl acetate, ethyl acetate, methyl propionate, methyl butyrate, methyl valerate, methyl caproate. Examples of the aliphatic hydrocarbons include straight chain or branched ones having 6 to 12 carbon atoms and hexane, heptane and petroleum ether are preferable. Examples of the alicyclic hydrocarbons include unsubstituted or substituted alicyclic hydrocarbons having 6 to 12 carbon atoms and cyclohexane, methylcyclohexane and cyclooctane are particularly suitable. Examples of the aromatic hydrocarbon include unsubstituted or substituted ones having 6 to 12 carbon atoms, and benzene, toluene and xylene are preferable. Further, examples of the halogenated hydrocarbons include chlorides, bromides and iodides of straight chain or branched alkanes having 1 to 8 carbon atoms, and chloroform, carbon tetrachloride and methylene chloride are preferable. Furthermore, straight chain or branched lower alcohols having 1 to 5 carbon atoms such as methanol and ethanol may be used therefor.

These organic solvent can be used either alone or a mixture of two or more of these.

In the alkali metal carboxylate, the alkaline earth metal carboxylate, the mixture of the carboxylic acid and the alkali metal salt or the mixture of the carboxylic acid an the alkaline earth metal salt to be used in the production of modified phospholipids, the carboxylic acid may be selected from among straight chain or branched aliphatic carboxylic acid having 2 to 8 carbon atoms and aromatic carboxylic acids having 7 to 12 carbon atoms (for example, aliphatic carboxylic acids such as acetic acid, butyric acid and propionic acid and aromatic carboxylic acid such as benzoic acid). Among these carboxylic acids, aliphatic ones are preferable. Examples of the alkali metal include sodium and potassium while examples of the alkaline earth metal include barium, magnesium and calcium. As the alkali metal salt or the alkaline earth metal salt, halides, carbonates and phosphates of these metals are available in the present invention.

In the production of the modified phospholipids of the present invention, the pH value of the reaction mixture is an important factor. Thus the reaction may be preferably conducted within a pH range of from 4.0 to 7.5, more preferably at pH 6.0±0.5.

Now a preferable method for the production of PA will be described below.

An enzyme capable of hydrolyzing a phospholipid into PA and a nitrogen-containing base and another enzyme capable of hydrolyzing a phospholipid into a diglyceride and a phosphoryl base are simultaneously or separately added to a phospholipid (for example, commercially available vegetable or animal defatted lecithin, commercially available crude lecithin).

Alternatively, in stead of the above-mentioned enzymes, the phospholipid is mixed with 10 to 100% by weight, based on the phospholipid, of the ground matter of the oilseed or the extract of the ground matter of the oilseed of at a ratio by weight of from 1.0 to 50 (preferably from 1.0 to 10) based on the phospholipid and the obtained mixture is formulated into a slurry by stirring.

Next, an alkyl carboxylate, preferably a lower alkyl (having 1 to 3 carbon atoms) ester of acetic acid or propionic acid, is added thereto at a ratio by weight of from 0.5 to 20 (preferably from 1.0 to 10) based on the phospholipids so as to initiate the reaction.

In stead of, or in addition to the above-mentioned organic solvent, an aqueous solution containing at least one substance selected from the group consisting of an alkali metal carboxylate, an alkaline earth metal carboxylate, a mixture of a carboxylic acid and an alkali metal salt, and a mixture of a carboxylic acid and an alkaline earth metal salt at a concentration of form 0.05 to 1.0M (preferably from 0.1 to 0.5M) (simply called a "reaction solution" hereinafter) is added to the phospholipid at a ratio by weight of from 1.0 to 30 (preferably from 2.0 to 10) based on the phospholipid, so as to induce the reaction.

The enzymatic activities of the treatment product of the oilseed or the two enzymes to be used in the present invention may preferably comprise from 0.01 to 1000 U (more preferably from 0.1 to 500 U) of the enzyme capable of hydrolyzing a phospholipid into PA and a nitrogen-containing base and from 0.01 to 1000 U (more preferably from 0.1 to 500 U) of the enzyme capable of hydrolyzing a phospholipid into a diglyceride and a phosphoryl base, each based on gram of the phospholipids to be used in the reaction.

When the above-mentioned two enzymes are to be used, they may be added either simultaneously or separately. When they are to be separately added, the order of the addition is not specified.

In the case of the enzyme capable of hydrolyzing a phospholipid into PA and a nitrogen-containing base, the expression "1 U" as used herein means the amount of the enzyme of hydrolyzing 1 μmol of phosphatidylcholine within 1 minute. In the case of the enzyme capable of hydrolyzing a phospholipid into a diglyceride and a phosphoryl base, on the other hand, the expression "1 U" as used herein means the amount of said enzyme capable of hydrolyzing 1 μmol of phosphatidylcholine within 1 minute.

In order to further elevate the enzymatic activities of the ground matter of the oilseed, 0.1 to 10% by weight (preferably 0.1 to 5% by weight), based on the starting phospholipids, of a plant growth promoter (for example, growth hormones such as gibberellin, auxin such as indoleacetic acid; halides, carbonates, phosphates and sulfates of typical divalent ions such as calcium or barium ion and/or transition metal ions such as manganese, lanthanum or cerium) may be added thereto, if required.

The reaction mixture is stirred at a reaction temperature of from 10° to 60° C., in particular, from 20° to 50° C. for several hours or longer so as to complete the reaction.

When the organic solvent and the aqueous solution containing at least one substance selected from the group consisting of the alkali metal carboxylate, the alkaline earth metal carboxylate, the mixture of the carboxylic acid and the alkali metal salt and the mixture of the carboxylic acid and the alkaline earth metal salt are used in a combination of these in the production of modified phospholipids, the weight ratio of the organic solvent/the aqueous solution containing at least one substance selected from the group consisting of the alkali metal carboxylate, the alkaline earth metal carboxylate, the mixture of the carboxylic acid and the alkali metal salt and the mixture of the carboxylic acid and the alkaline earth metal salt is 0.5 to 20/1.0 to 30, preferably 1.0 to 10/2.0 to 10.

A preferred combination of the organic solvent with aqueous solution containing at least one substance selected from the group consisting of alkali metal carboxylate, the alkaline earth metal carboxylate, the mixture of the carboxylic acid and the alkali metal salt and the mixture of the carboxylic acid and the alkaline earth metal salt is a combination of mixed solvent of an alkyl carboxylate and an aliphatic hydrocarbon with a buffer solution containing the alkaline earth metal salt.

When the organic solvent is used alone as the solvent in the production of modified phospholipids, water may be additionally added to the reaction system at a ratio by weight of from 1.0 to 30, preferably 2.0 to 10, based on the phospholipids.

In the present invention, the procedure is never restricted in detail. Namely, the order of the addition of the substances to be used in the reaction including the starting phospholipids, solvent, the ground matter of the oilseed or the extract thereof and the compositions of the solvent and reaction mixture to be used are never restricted. They may be arbitrarily selected so as to achieve the effects of the present invention.

The PA formed by the process of the present invention may be easily isolated and collected from the reaction slurry by a conventional purification method such as solvent extraction or solvent fractionation.

The process of the hydrolysis reaction of the phospholipids according to the present invention may be monitored by, for example, thin layer chromatography (TLC) or high performance liquid chromatography (HPLC). Further the reaction time may be controlled thereby.

According to the present invention, the target PA may be obtained under mild conditions (e.g., at a room temperature, under the atmospheric pressure, at a neutral pH value) at a high purity and a high yield.

Furthermore, the present invention can give a noteworthy effect. That is, the diglyceride formed as a side product from the phospholipids during the process of the present invention serves as an excellent solubilizer for the PA. This solubilizing effect of the diglyceride on PA widens the application range of PA to various fat products and considerably improves the functions of fat products.

According to the present invention, therefore, PA of a high purity and a high solubility in fats can be easily produced on an industrial scale.

To further illustrate the present invention, and not by way of limitation, the following Examples and Comparative Examples will be given.

REFERENCE EXAMPLE 1

Preparation of a Ground Matter of an Oilseed

Soybean was employed as an oilseed. 200 g of soybean harvested in U.S.A. (Ohio, Glycine max [L.]) was ground in a Waring Blender. The ground matters were sieved (mesh No. 20) so as to remove contaminants. The ground soybeans thus obtained were used in the following Examples.

REFERENCE EXAMPLE 2

Preparation of an Extract of an Ground Matter of an Oilseed 25 g of soybean harvested in U.S.A. (silky bean) was added to 150 g of a 0.1M sodium acetate/acetic acid buffer (pH 6.0) containing 50 mM of calcium chloride and wet-ground at a room temperature so as to give a diameter of 2 mm or below and centrifuged at 3,000 rpm for 10 minutes. Thus 120 g of a supernatant (extract) was obtained. The extract thus obtained was used in the following Examples.

REFERENCE EXAMPLE 3

Preparation of a Ground Matter of an Oilseed

Lipoxygenase-deficient soybean was used as the oilseed. As the lipoxygenase-deficient soybean, that lacking both of lipoxygenase-2 (L-2) and lipoxygenase-3 (L-3) disclosed in Nippon Jozo Kyokaishi, vol. 82, No. 2, 76 to 79 (1987), was employed. 25 g of the lipoxygenase-deficient soybean was ground in a Waring Blender and the ground matters were sieved (mesh No. 20) to thereby remove contaminants. The ground soybeans thus obtained were used in the following Examples.

REFERENCE EXAMPLE 4

25 g of the lipoxygenase-deficient soybeans used in Referential Example 3 were added to 150 g of a 0.1M sodium acetate/acetic acid buffer solution (pH 6.0) containing 50 mM of calcium chloride. Then the soybeans were wet-ground at a room temperature so as to give a diameter of 2 mm or below and centrifuged at 3,000 rpm for 10 minutes to thereby give 120 g of a supernatant (extract). The extract thus obtained was used in the following Examples.

EXAMPLE 1

20 g of commercially available defatted lecithin (manufactured by Tsuru Lecithin Kogyo K.K.) was introduced into a 500 ml four-neck flask equipped with a stirrer. 1250 ml of a 0.1M tris-hydrochloride buffer solution (pH 6.0-8.0) was added thereto. Further, 340 ml of hexane/ethyl acetate (2/1 (v/v)) was added and the mixture was stirred. Furthermore, 150 ml of a 1M aqueous solution of calcium chloride was added thereto. Subsequently, 150 ml of an aqueous solution of PL-D of a microbial origin (manufactured by Toyo Jozo Co., Ltd., originating from *Streptomyces chromofuscus*) and PI-specific PL-C (manufactured by Sapporo Breweries, Ltd., originating from *Bacillus Turingenesis*) (15 and 3 U per gram of the phospholipid, respectively) was added thereto. The reaction mixture was stirred for 14 hours while maintaining the temperature at 30° C. After the completion of the reaction, the reaction mixture was allowed to stand so as to separate the solvent phase. Then the solvent was distilled off from the solvent phase under reduced pressure.

The PA content of the phospholipids (17 g) thus obtained was determined by HPLC (UV detection type).

Further, the solubility of the phospholipid in a fat was examined by the following manner.

A fat composition comprising 95% by weight of a marketed salad oil and 5% by weight of the phospholipid thus obtained was allowed to stand at 25° C. for 24 hours. Then, the state of the oil composition was visually observed and evaluated by the criterion indicated below:

A: Transparent, without any turbidness.
B: Slightly turbid.
C: Fine particles were precipitated.

Table 1 shows the results.

EXAMPLE 2

The reaction of Example 1 was repeated except that the PL-D was employed alone. The solvent phase was separated and the solvent was distilled off therefrom. Then the product (20 g) was dispersed and dissolved in 90 ml of a 0.1M borate buffer solution (pH 7.5) and PI-specific PL-C was added. The obtained mixture was allowed to react at 37° C. for 20 hours. The reaction mixture was extracted with chloroform/methanol (2/1 (v/v)) twice and the extract was subjected to Folch partition. The chloroform/methanol was removed to thereby give 12 g of a phospholipid product. The PA content of the obtained phospholipids was determined by HPLC (UV detection type). Further, the solubility of the phospholipid thus obtained was examined and evaluated as in Example 1.

Table 1 shows the results.

EXAMPLES 3 TO 5

The reaction of Example 1 was repeated except that the PL-C employed in Example 1 was replaced with phosphodiesterase (manufactured by Wako Pure Chemicals Co., Ltd., originating from Crotalidae snake venom) (Example 3), acid phosphatase (manufactured by Fluka AG, originating from wheat germ) (Example 4) and alkali phosphatase (manufactured by Wako Pure Chemicals Co., Ltd., originating from calf intestine) (Example 5). In each case, a 0.1M tris-hydrochloride buffer solution (pH 8.8), a 0.1M acetate buffer solution (pH 5.0) and a 0.5M tris-hydrochloride buffer solution (pH 9.0), respectively, were used. Each enzyme was used at ratios of 0.5, 5 and 50 U/g, respectively, of phospholipid. The PA content in the phospholipids thus obtained was determined by HPLC (UV detection type). Further, the solubilities of the phospholipids thus obtained were examined and evaluated as in Example 1.

Table 1 shows the results.

EXAMPLE 6

Each 200 U of the PL-D and PL-C as used in Example 1 were fixed on 1 g of a weakly basic anion exchange resin through a covalent bond method so as to give fixed PL-D and PL-C. Then the procedure of Example 1 was repeated except that the PL-D and PL-C were replaced with these fixed enzymes. Further, the solubility of the phospholipid thus obtained was examined and evaluated as in Example 1.

Table 1 shows the results.

COMPARATIVE EXAMPLE 1

20 g of commercially available defatted lecithin (manufactured by Tsuru Lecithin Kogyo K.K.) was introduced into a 500 ml four-neck flask equipped with a stirrer. 1250 ml of a 0.1M tris-hydrochloride buffer solution (pH 8.0) was added thereto. Further 340 ml of ether was added followed by stirring. 150 ml of an aqueous solution of calcium chloride (1M) was further added thereto and then 150 ml of an aqueous solution of phospholipase D of a microbial origin (manufactured by Toyo Jozo Co., Ltd., originating from *Streptomyces chromofuscus*) was added thereto (15 U/g of phospholipid). The reaction mixture was stirred for 14 hours while maintaining the reaction temperature at 30° C. After the completion of the reaction, the reaction mixture was allowed to stand to thereby separate the ether phase. The ether was distilled off from the ether phase under reduced pressure. The composition of the phospholipids (17 g) thus obtained wa identified by HPLC (UV detection type). Further, the solubility of the phospholipid thus obtained was examined and evaluated as in Example 1.

Table 1 shows the results.

TABLE 1

| Sample | PA content in phospholipids* (% by weight) | Solubility of the phospholipid |
|---|---|---|
| Example 1 | 95.3 | A |
| Example 2 | 95.0 | A |
| Example 3 | 95.0 | A |
| Example 4 | 95.1 | A |
| Example 5 | 94.8 | A |
| Example 6 | 94.8 | A |
| Comparative Example 1 | 70.0 | C |
| Marketed lecithin | 18.0 | B |

Note: *Determined by HPLC.

As can be seen in Table 1 above, the phospholipids of Comparative Example 1 showed a poor solubility and a considerable amount of a precipitate. In contrast thereto, the phospholipids of the present invention (Examples 1 to 6) showed each a high solubility without showing any precipitate.

EXAMPLE 7

25 g of commercially available defatted lecithin (SLP-WSP, trade name, manufactured by Tsuru Lecithin Kogyo K.K.) was introduced into a 500 ml four-neck flask equipped with a stirrer. 25 g of the ground soybeans prepared in Reference Example 1 were added thereto. Then 250 ml of ethyl acetate was added to the obtained mixture under stirring. Further, 32.5 g of deionized water was added thereto while continuing the stirring. The reaction mixture was stirred at 30° C. for 20 hours.

The ethyl acetate phase (A) was removed from the reaction mixture and the residue (B) was extracted with chloroform/methanol (2/1 (v/v)) twice. The extract containing (B) was subjected to Folch partition and combined with the residue obtained by removing the ethyl acetate from the above-mentioned (A). After removing the chloroform/methanol, a crude phospholipid product (C) was obtained. Five times by volume as much as (C) of acetone was added thereto and the obtained mixture was stirred and then allowed to stand. Thus 21 g of a precipitate (D) was obtained. (D) was washed with ice-cooled acetone and dried under reduced pressure. The phospholipid composition of (D) was identified by HPLC (UV detection type). Table 2 shows the results.

EXAMPLE 8

25 g of commercially available defatted lecithin (SLP-WSP, trade name, manufactured by Tsuru Lecithin Kogyo K.K.) was introduced into a 500 ml four-neck flask equipped with a stirrer. 25 g of the ground soybeans prepared in Reference Example 1 were added thereto. Then 100 ml of a 0.1M sodium acetate/acetic acid buffer solution (pH 6.0) and 32.5 g of a 50 mM aqueous solution of calcium chloride were added to the obtained mixture under stirring. The reaction mixture was further stirred at 30° C. for 20 hours.

The residue (B) was taken out from the reaction mixture and extracted with chloroform/methanol (2/1 (v/v)) twice. The extract containing (B) was subjected to Folch partition and the chloroform/methanol was removed so as to give a crude phospholipid product (G). Five times by volume as much as (G) of acetone was added thereto and the obtained mixture was stirred and then allowed to stand. Thus 21 g of a precipitate (H) was obtained. (H) was washed with ice-cooled acetone and dried under reduced pressure. The phospholipid composition of was identified by HPLC (UV detection type). Table 2 shows the results.

TABLE 2

| Sample | Phospholipid composition* | | | | |
|---|---|---|---|---|---|
| | PC** (%) | LPC** (%) | PE** (%) | PI** (%) | PA** (%) |
| Example 7 (D) | 1.8 | 0.4 | 0.7 | 1.6 | 95.3 |
| Example 8 (H) | 1.8 | 0.4 | 0.7 | 1.6 | 95.3 |
| Comparative Example 1 | 5.0 | 0.5 | 3.0 | 18.7 | 70.0 |
| Marketed lecithin | 33.0 | 1.0 | 33.0 | 15.0 | 18.0 |

*Determined by HPLC (indicated in % by weight).
**LPC lysophosphatidylcholine; PC, PE, PI and PA: as defined above.

EXAMPLE 9

The hydrolysis process of Example 7 was repeated except that the soybean employed as the oilseed was replaced by rapeseed, sunflower seed, peanut, olive seed and corn, each in the same amount (weight) as that of the soybean. The composition of each modified phospholipids thus obtained is given in Table 3.

EXAMPLE 10

The hydrolysis process of Example 8 was repeated except that the soybean employed as the oilseed was replaced by rapeseed, sunflower seed, peanut, olive seed and corn, each in the same amount (weight) as that of the soybean. The composition of each modified phospholipids thus obtained is given in Table 3.

COMPARATIVE EXAMPLE 2

The hydrolysis process of Example 9 was repeated except that the oilseed was replaced by a vegetable juice, which had been obtained by filtering ground cabbages, in the same amount (weight) as that of the soybeans. The composition of the modified phospholipids thus obtained is given in Table 3.

COMPARATIVE EXAMPLE 3

The hydrolysis process of Example 10 was repeated except that the oilseed was replaced by a vegetable juice, which had been obtained by filtering ground cabbages, in the same amount (weight) as that of the soybeans. The composition of the modified phospholipids thus obtained is given in Table 3.

TABLE 3

(Comparison of the ground matter of the oilseed*)

| Sample | Phospholipid composition* | | | | |
|---|---|---|---|---|---|
| | PC** (%) | LPC** (%) | PE** (%) | PI** (%) | PA** (%) |
| Rapeseed | | | | | |
| Example 9 | 10.4 | 0.8 | 0.3 | 1.4 | 86.1 |
| Example 10 | 3.0 | 0.6 | 1.6 | 7.5 | 86.5 |
| Sunflower | | | | | |
| Example 9 | 5.0 | 0.2 | 5.8 | 6.0 | 82.3 |
| Example 10 | 6.1 | 0.3 | 6.0 | 6.0 | 81.6 |
| Peanut | | | | | |
| Example 9 | 3.8 | 0.6 | 11.0 | 1.7 | 80.9 |
| Example 10 | 4.0 | 0.6 | 10.0 | 5.0 | 80.0 |
| Olive | | | | | |
| Example 9 | 4.0 | 0.7 | 9.8 | 5.0 | 80.4 |
| Example 10 | 3.8 | 0.6 | 1.3 | 7.0 | 80.5 |
| Corn | | | | | |
| Example 9 | 4.0 | 0.5 | 7.9 | 3.5 | 83.0 |
| Example 10 | 4.0 | 0.5 | 8.0 | 4.0 | 80.0 |
| Cabbage | | | | | |
| Comparative Example 2 | 20.0 | 1.5 | 25.5 | 16.0 | 36.0 |
| Comparative Example 3 | 20.0 | 1.0 | 25.0 | 16.0 | 38.0 |
| Marketed lecithin (SLP-WSP) | 33.0 | 1.0 | 33.0 | 15.0 | 18.0 |

*,**As defined in Table 2.

EXAMPLE 11

25 g of commercially available defatted lecithin (SLP-WSP, trade name, manufactured by Tsuru Lecithin Kogyo K.K.) was introduced into a 500 ml four-neck flask equipped with a stirrer. Then 120 g of an extract of ground soybeans prepared in Reference Example 2 was added thereto. 250 ml of ethyl acetate was added to the obtained mixture under stirring. Further 32.5 g of water was added thereto and the stirring was continued. The reaction mixture was stirred at 30° C. for 20 hours.

The ethyl acetate phase (A) was removed from the reaction mixture and the residue (B) was extracted with chloroform/methanol (2/1 (v/v)) twice. The extract containing (B) was subjected to Folch partition and combined with the residue obtained by removing the ethyl acetate from the above-mentioned (A). After removing the chloroform/methanol, a crude phospholipid product (C) was obtained. Five times by volume as much as (C) of acetone was added and the resulting mixture was stirred followed by allowing to stand. Thus 21 g of a precipitate (D) was obtained. The PA content in the obtained (D) was determined by HPLC (UV detection type). Table 4 shows the results.

EXAMPLE 12

25 g of commercially available defatted lecithin (SLP-WSP, trade name, manufactured by Tsuru Lecithin Kogyo K.K.) was introduced into a 500 ml four-neck flask equipped with a stirrer. Then 120 g of an extract of ground soybeans prepared in Reference Example 2 was added thereto. 100 ml of a 0.1M sodium acetate/acetic acid buffer solution (pH 6.0) and 32.5 g of a 50 mM aqueous solution of calcium chloride was added to the mixture as reaction solutions under stirring. The reaction mixture was further stirred at 30° C. for 20 hours.

The residue (B) was collected from the reaction mixture and extracted with chloroform/methanol (2/1 (v/v)) twice. The extract containing (B) was subjected to Folch partition and chloroform/methanol was removed. Thus a crude phospholipid product (G) was obtained. Five times by volume as much as (G) of acetone was added and the resulting mixture was stirred followed by allowing to stand. Thus 21 g of a precipitate (H) was obtained. The obtained (H) was further washed with ice-cooled acetone and dried under reduced pressure. The PA content in the obtained (H) was determined by HPLC (UV detection type). Table 4 shows the results.

TABLE 4

| Sample | PA content in phospholipids* (% by weight) |
|---|---|
| Example 11 (D) | 95.3 |
| Example 12 (H) | 95.3 |
| Comparative | 70.0 |

TABLE 4-continued

| Sample | PA content in phospholipids* (% by weight) |
|---|---|
| Example 1 | |
| Marketed lecithin | 18.0 |

Note; *Determined by HPLC.

EXAMPLE 13

The hydrolysis process of Example 11 was repeated except that the soybeans employed in Reference Example 2 as the oilseed was replaced by rapeseed, sunflower seed, peanut, olive seed and corn, each in the same amount (weight) as that of the soybean. The PA content in each modified phospholipids thus obtained is given in Table 5.

EXAMPLE 14

The hydrolysis process of Example 13 was repeated except that the soybeans employed in Reference Example 2 as the oilseed was replaced by extracts of ground rapeseed, sunflower seed, peanut, olive seed and corn, each in the same amount (weight) as that of the soybean. The PA content in each modified phospholipids thus obtained is given in Table 5.

COMPARATIVE EXAMPLE 4

The hydrolysis process of Example 13 was repeated except that the extract of the oilseed was replaced by a vegetable juice, which had been obtained by filtering ground cabbages, in the same amount (weight) as that of the extract of soybeans. The PA content in the phospholipids thus obtained is given in Table 5.

COMPARATIVE EXAMPLE 5

The hydrolysis process of Example 14 was repeated except that the extract of the oilseed was replaced by a vegetable juice, which had been obtained by filtering ground cabbages, in the same amount (weight) as that of the extract of soybeans. The PA content in the phospholipids thus obtained is given in Table 5.

TABLE 5

(Comparison of the ground matter of the oilseed)

| Sample | PA content in phospholipids* (% by weight) |
|---|---|
| Rapeseed | |
| Example 13 | 86.1 |
| Example 14 | 86.5 |
| Sunflower | |
| Example 13 | 82.3 |
| Example 14 | 81.6 |
| Peanut | |
| Example 13 | 80.9 |
| Example 14 | 80.0 |
| Olive | |
| Example 13 | 80.4 |
| Example 14 | 80.5 |
| Corn | |
| Example 13 | 83.0 |
| Example 14 | 80.0 |
| Cabbage | |
| Comparative Example 4 | 36.0 |
| Comparative Example 5 | 38.0 |
| Marketed lecithin (SLP-WSP) | 18.0 |

Note; *Determined by HPLC.

EXAMPLE 15

25 g of commercially available defatted lecithin (SLP-WSP, trade name, manufactured by Tsuru Lecithin Kogyo K.K.) was introduced into a 500 ml four-neck flask equipped with a stirrer. 25 g of the ground soybeans lacking both of L-2 and L-3 prepared in Reference Example 3 were added thereto. Then 250 ml of ethyl acetate wa added to the obtained mixture under stirring. Further, 32.5 g of water was added thereto while continuing the stirring. The reaction mixture was stirred at 30° C. for 20 hours.

The ethyl acetate phase (A) was removed from the reaction mixture and the residue (B) wa extracted with chloroform/methanol (2/1 (v/v)) twice. The extract containing (B) was subjected to Folch partition and combined with the residue obtained by removing the ethyl acetate from the above-mentioned (A). After removing the chloroform/methanol, a crude phospholipid product (C) was obtained. Five times by volume as much as (C) of acetone was added thereto and the obtained mixture was stirred and then allowed to stand. Thus 21 g of a precipitate (D) was obtained. (D) was washed with ice-cooled acetone and dried under reduced pressure. The PA content in (D) was determined by HPLC (UV detection type). Table 6 shows the results.

EXAMPLE 16

25 g of commercially available defatted lecithin (SLP-WSP, trade name, manufactured by Tsuru Lecithin Kogyo K.K.) was introduced into a 500 ml four-neck flask equipped with a stirrer. 25 g of the ground soybeans lacking both of L-2 and L-3 prepared in Reference Example 3 were added thereto. Then 100 ml of a 0.1M sodium acetate/acetic acid buffer solution (pH 6.0) and 32.5 g of a 50 mM aqueous solution of calcium chloride were added to the obtained mixture under stirring. The reaction mixture was further stirred at 30° C. for 20 hours.

The residue (E) was taken out from the reaction mixture and extracted with chloroform/methanol (2/1 (v/v)) twice. The extract containing (E) was subjected to Folch partition and the chloroform/methanol was removed so as to give a crude phospholipid product (F). Five times by volume as much as (F) of acetone was added thereto and the obtained mixture was stirred and then allowed to stand. Thus 20 g of a precipitate (G) was obtained. (G) was washed with ice-cooled acetone and dried under reduced pressure. The PA content in (G) was determined by HPLC (UV detection type).

Table 6 shows the results.

TABLE 6

| Sample | PA content in phospholipids* (% by weight) |
|---|---|
| Example 15 | 96.0 |
| Example 16 | 95.0 |

Note; *Determined by HPLC.

Fats containing these phospholipids were used in cooking and the dishes (for example, fries, salads) were evaluated. As a result, those prepared with the use of the phospholipids of Examples 15 and 16 of the present invention showed excellent tastes and no offensive odor.

EXAMPLE 17

The hydrolysis process of Example 15 was repeated except that the ground lipoxygenase-deficient soybeans employed in Example 15 were replaced with 120 g of the extract of ground lipoxygenase-deficient soybeans obtained in Reference Example 4. Analysis was conducted in the same manner as the one described in Example 15.

Table 7 shows the results.

EXAMPLE 18

The hydrolysis process of Example 16 was repeated except that the ground lipoxygenase-deficient soybeans obtained in Reference Example 3 were replaced with 120 g of the extract of ground lipoxygenase-deficient soybeans obtained in Reference Example 4. Analysis was conducted in the same manner as the one described in Example 16.

Table 7 shows the results.

TABLE 7

| Sample | PA content in phospholipids* (% by weight) |
|---|---|
| Example 17 | 96.0 |
| Example 18 | 95.8 |

Note: *Determined by HPLC.

Fats containing these phospholipids were used in cooking and the dishes (for example, fries, salads) were evaluated. As a result, those prepared with the use of the phospholipids of Examples 11 and 12 of the present invention showed excellent tastes and no offensive odor.

While the invention has been described in detail and with reference to specific examples thereof, it will be apparent to one skilled in the art that various changes and modifications can be made therein without departing from the spirit and scope thereof.

What is claimed is:

1. A process for producing phosphatidic acid which comprises treating phospholipids with an enzyme capable of hydrolyzing a phospholipid into phosphatidic acid and a nitrogen-containing base and another enzyme capable of hydrolyzing a phospholipid into a diglyceride and a phosphoryl base; and recovering said phosphatidic acid.

2. A process as claimed in claim 1, wherein said enzyme capable of hydrolyzing a phospholipid into phosphatidic acid and a nitrogen-containing base is phospholipase D.

3. A process as claimed in claim 1, wherein said enzyme capable of hydrolyzing a phospholipid into a diglyceride and a phosphoryl base is at least one selected from the group consisting of phospholipase C, phosphodiesterase and acid phosphatase.

4. A process for producing phosphatidic acid, which comprises:

(1) treating phospholipids with an enzyme capable of hydrolyzing a phospholipid into phosphatidic acid and a nitrogen-containing base and another enzyme capable of hydrolyzing a phospholipid into a diglyceride and a phosphoryl base in a buffer comprising an organic solvent, an aqueous solution or a mixture of an organic solvent and an aqueous solution containing at least one substance selected from the group consisting of an alkali metal carboxylate, an alkaline earth metal carboxylate, a mixture of a carboxylic acid and an alkali metal salt and a mixture of a carboxylic acid and an alkaline earth metal salt; and (2) isolating said phosphatidic acid from the reaction mixture.

5. A process as claimed in claim 4, wherein said organic solvent is at least one compound selected from the group consisting of an alkyl carboxylate, an alkane, an aliphatic hydrocarbon, an aromatic hydrocarbon and a halogenated hydrocarbon, each having a melting point of 40° C. or below.

6. A process as claimed in claim 4, wherein said organic solvent is used at a ratio by weight of from 0.5 to 10 based on the phospholipids.

7. A process as claimed in claim 4, wherein said carboxylic acid is at least one compound selected from the group consisting of an aliphatic carboxylic acid having 2 to 8 carbon atoms and an aromatic carboxylic acid having 7 to 12 carbon atoms.

8. A process as claimed in claim 4, wherein said aqueous solution containing at least one substance selected from the group consisting of an alkali metal carboxylate, an alkaline earth metal carboxylate, a mixture of a carboxylic acid and an alkali metal salt and a mixture of a carboxylic acid and an alkaline earth metal salt at a concentration of from 0.05 to 1.0M is used at a ratio by weight of from 1.0 to 30 based on the phospholipids.

9. A process as claimed in claim 4, wherein said treatment is conducted at a temperature of from 10° to 60° C.

10. A process as claimed in claim 4, wherein said treatment is conducted at a pH value of from 4.0 to 7.5.

11. A process as claimed in claim 4, wherein enzyme activities in the reaction system comprise from 0.01 to 1000 U of an enzyme capable of hydrolyzing a phospholipid into phosphatidic acid and a nitrogen-containing base and from 0.01 to 1000 U of another enzyme capable of hydrolyzing a phospholipid into a diglyceride and a phosphoryl base, each per gram of the phospholipids.

12. A process for producing phosphatidic acid, which comprises treating phospholipids with an enzyme from an oilseed selected from a ground oilseed or an extract of an oilseed in a buffer comprising an organic solvent, an aqueous solution or a mixture of an organic solvent and an aqueous solution containing at least one substance selected from the group consisting of an alkali metal carboxylate, an alkaline earth metal carboxylate, a mixture of a carboxylic acid and an alkali metal salt and a mixture of a carboxylic acid and an alkaline earth metal salt; and recovering said phosphatidic acid.

13. A process as claimed in claim 12, wherein said organic solvent is at least one compound selected form the group consisting of an alkyl carboxylate, an alkane, an aliphatic hydrocarbon, an aromatic hydrocarbon, a halogenated hydrocarbon or a mixture of these, each having a melting point of 40° C. or below.

14. A process as claimed in claim 12, wherein said organic solvent is used at a ratio by weight of from 0.5 to 10 based on the phospholipids.

15. A process as claimed in claim 12, wherein said carboxylic acid is at least one compound selected from the group consisting of an aliphatic carboxylic acid having 2 to 8 carbon atoms in total and an aromatic carboxylic acid having 7 to 12 carbon atoms in total.

16. A process as claimed in claim 12, wherein said aqueous solution containing at least one substance selected from the group consisting of an alkali metal carboxylate, an alkaline earth metal carboxylate, a mixture of a carboxylic acid and an alkali metal salt and a mixture of a carboxylic acid and an alkaline earth metal salt at a concentration of from 0.05 to 1.0M is used at a ratio by weight of from 1.0 to 30 based on the phospholipids.

17. A process as claimed in claim 12, wherein said treatment is conducted at a temperature from 10° to 60° C.

18. A process as claimed in claim 12, wherein said treatment is conducted at a pH value of from 4.0 to 7.5.

19. A process as claimed in claim 12, wherein said ground matter is used in an amount of 10 to 100% by weight based on the phospholipids.

20. A process as claimed in claim 12, wherein the enzyme activities of said ground matter comprise from 0.01 to 1000 U of an enzyme capable of hydrolyzing a phospholipid into phosphatidic acid and a nitrogen-containing base and from 0.01 to 1000 U of another enzyme capable of hydrolyzing a phospholipid into a diglyceride and a phosphoryl base, each per gram of the phospholipids.

21. A process as claimed in claim 12, wherein said extract is prepared by extracting said oilseed with water or an aqueous solution containing at least one compound selected from the group consisting of an alkali metal carboxylate, an alkali metal salt and an alkaline earth metal salt.

22. A process as claimed in claim 12, wherein said extract is used at a ratio by weight of from 1.0 to 50 based on the phospholipids.

23. A process as claimed in claim 12, wherein the enzyme activities of said extract comprise from 0.01 to 1000 U of an enzyme capable of hydrolyzing a phospholipid into phosphatidic acid and a nitrogen-containing base and from 0.01 to 1000 U of another enzyme capable of hydrolyzing a phospholipid into a diglyceride and a phosphoryl base, each per gram of the phospholipids.

24. A process as claimed in claim 12, wherein said oilseed is selected from a group consisting of soybean, rapeseed, sunflower seed, peanut, cotton seed, safflower seed, mustard seed, sesame, olive seed and corn.

25. A process as claimed in claim 24, wherein said oilseed is collected from a lipoxygenase-deficient plant.

26. A process as claimed in claim 25, wherein said oilseed collected from a lipoxygenase-deficient plant is a lipoxygenase-deficient soybean.

* * * * *